United States Patent [19]
Hodgson

[11] Patent Number: 5,606,979
[45] Date of Patent: Mar. 4, 1997

[54] GUIDE WIRE

[75] Inventor: William S. Hodgson, Cohasset, Mass.

[73] Assignee: The MicroSpring Company Inc., Norwell, Mass.

[21] Appl. No.: 69,050

[22] Filed: May 28, 1993

[51] Int. Cl.⁶ ...................................................... A61B 6/00
[52] U.S. Cl. ............................. 128/772; 128/657; 29/234
[58] Field of Search ..................................... 128/657, 772; 604/164, 265, 280, 282, 95; 29/234, 235, DIG. 29

[56]          References Cited
            U.S. PATENT DOCUMENTS

| 3,841,308 | 10/1974 | Tate | 128/772 |
| 3,973,556 | 8/1976 | Fleischhackell | 128/772 |
| 4,080,706 | 3/1978 | Heilman et al. | 128/772 X |
| 4,884,579 | 12/1989 | Engelson | 128/657 X |
| 4,917,104 | 4/1990 | Rebell | 128/772 |
| 4,955,862 | 9/1990 | Sepetka | 604/280 X |
| 5,129,890 | 7/1990 | Bates et al. | 128/772 X |
| 5,171,383 | 12/1992 | Sagaye et al. | 128/772 X |
| 5,267,574 | 12/1993 | Viera et al. | 128/772 |

Primary Examiner—Sam Rimell
Attorney, Agent, or Firm—Hale and Dorr

[57] ABSTRACT

A method and apparatus for producing a guide wire including a core wire surrounded by a heat shrunk polymeric plastic sleeve of variable wall thickness. The core wire is inserted into the sleeve, and heat is applied to successive axially spaced annular zones of the sleeve to heat shrink it around the core. The distal portion of the sleeve and core wire are moved relative to the heat zones at one rate of speed, and the proximal portion of the sleeve is moved relative to the heat zones at a different rates of speed. The thickness of the heat shrunk sleeve is varied by controlling the rates of speed such that a variable and controlled tension is applied to the sleeve as it is being heat shrunk.

15 Claims, 3 Drawing Sheets

GUIDE WIRE

FIELD OF INVENTION

This invention relates to guide wires and, more particularly, to guide wires used to introduce catheters into human cardiovascular systems.

BACKGROUND OF INVENTION

There are in the art a number of flexible guide wires used in medical applications. Exemplary such devices are shown in U.S. Pat. Nos. 3,789,841, 4,538,622, 4,545,390, 4,721,117, and 4,884,579, all of which are hereby incorporated by reference. Some such devices, including those shown in U.S. Pat. Nos. 3,789,841, 4,721,117 and 4,884,579, include a plastic (e.g., Teflon) covering that surrounds at least a portion of the guide wire. In some of these devices, a constant diameter Teflon jacket surround the uniform diameter portion of the core wire; in some, a more tip portion is coated with Teflon or covered with a polymeric tube that is in turn Teflon coated; in some, the Teflon covering is sprayed on. The sprayed coatings are often are somewhat rough and prone to peeling; and both they and tubular sleeves typically undesirably increase the overall diameter of at least some portions of the overall guide wire.

SUMMARY OF INVENTION

The present invention provides a guide wire in which a continuous tube or sleeve is drawn (rather than sprayed or painted) over a substantial length of the core wire, from closely adjacent the distal tip to adjacent the proximal end. In preferred embodiments, the sleeve is applied by drawing a heat shrinkable tube over the core wire such that the thickness of the tube is controllable varied as it is applied, and the overall diameter of the guide wire assembly is maintained substantially constant.

DESCRIPTION OF PREFERRED EMBODIMENT

Figure 1:
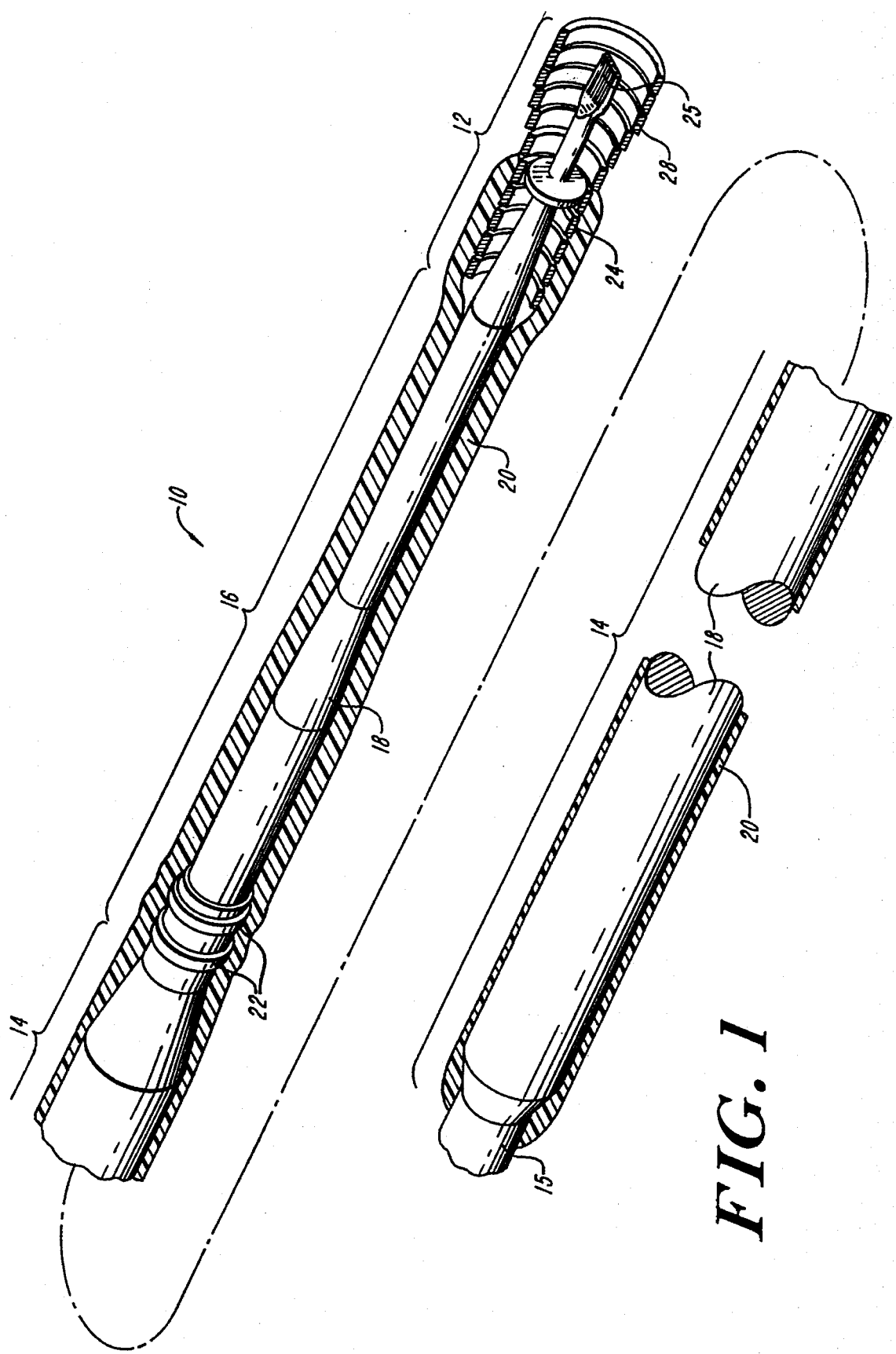
FIG. 1 is a perspective, sectional view of a guide wire assembly constructed in accord with the present invention.
Figure 2:
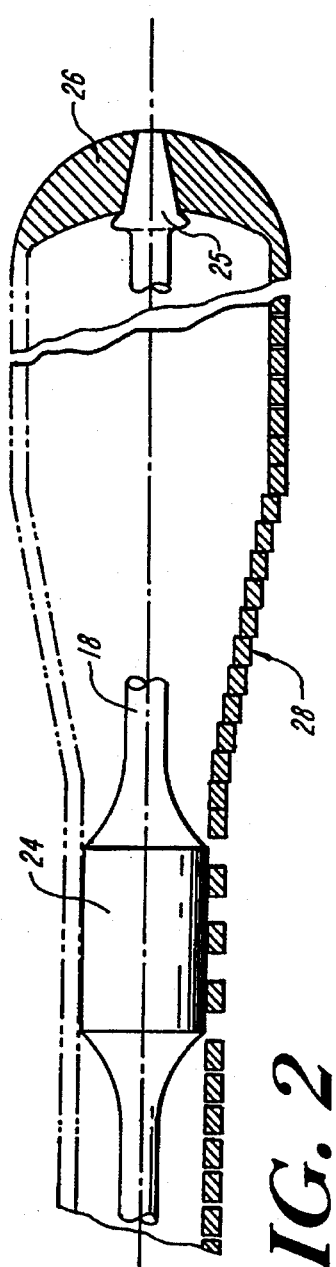
FIGS. 2 is a sectional view of portions of the core wire of the guide wire assembly of FIG. 1.

Reference is now made to FIGS. 1–2 which illustrate a guide wire, generally designated 10. It will be appreciated that the guide wire is almost 6' long and only about 0.014 in. in diameter, and that the horizontal and traverse scales of the drawings are thus different. As shown, guide wire 10 has a tip portion 12 about 2 inches long, a proximal portion 14 about 4½ feet long, and an distal portion 16 about 10 inches long. The maximum diameter of the complete wire assembly is 0.014 in.; current requirements are that, in field testing, it pass through an 0.014 in. diameter hole. The guide wire comprises a stainless steel core wire 18 that extends axially the length of the device and that, except in some of the tip portion 12, is covered by a plastic (e.g., Teflon) sleeve 20. The core wire 18 varies in diameter along its length; the overall diameter of the complete guide wire 10 is substantially constant.

Throughout most of proximal portion 14, core wire 18 has a substantially constant diameter of about 0.00128 in. The distal end of proximal portion 14 tapers to a diameter of about 0.010 in. before joining the distal portion 16. Adjacent its proximal end the diameter of core wire 18 tapers to about 0.010 in. and then continues at that diameter for about ½ inch to provide a reduced diameter section 15 for retaining the proximal end of sleeve 20.

The core wire 18 within distal portion 16 includes a number of axially-spaced portions arranged so that the overall diameter of the core wire decreases, in steps, from a 0.010 in. adjacent proximal portion 14 to about 0.0056 in. at the proximal end of tip portion 12. A short, 0.100 in. diameter section at the proximal end includes a plurality of annular locking grooves 22, having a radial depth of about 0.0010 in. The major length of the core wire in distal portion 16 has a diameter of about 0.007 inches, and the wire tapers towards the distal end to provide an about 3 inches long, 0.0056 inch diameter length at the proximal end of tip portion 12.

Approximately midway within the approximately two inch length of tip portion 12, core wire 18 includes an annular ring 24, about 0.0064 inches in diameter and 0.015 in. in axial length. On the proximal side of ring 24, the portion of the core wire within tip portion tapers from an initial diameter of about 0.0056 in. (where it joins distal portion 16) to about 0.003 inches at ring 24. Distal of ring 24, the core wire continues to taper to a diameter of about 0.0022 in. As shown, the distal end of the core wire, including part of the taper, is flattened to a thickness of about 0.0010 in. The flat portion 25 is secured, typically by gold brazing, to an essentially hemispherical tip 26 (as shown on FIG. 2) at the far distal end of the guide wire.

Tip portion 12 also includes a tapered spring 28 (shown most clearly in FIG. 2) of helically wrapped (about 660 turns) of platinum wire (about 0.0013 in. thick by 0.003 in. wide) that generally coaxially surrounds the length of core wire 18 within the tip portion. Spring 28 has an outer diameter of about 0.0139 in. at its distal end (where it is gold brazed to tip 26) and tapers to provide a diameter about 0.0104 in. from approximately its mid-point (where it is gold brazed to ring 24) to its proximal end.

As previously mentioned, Teflon sleeve 20 varies in thickness. Along most of the length of core wire 18 in proximal portion 14, the sleeve is about 0.0002 to about 0.0004 inches (preferably about 0.0003 inches) thick, so that it adds not more than about 0.0008 (and preferably only about 0.0006) inches to the overall diameter of the core wire 18, and the overall diameter of the guide wire 10 in the proximal portion will not be more than 0.014 (and preferably will not be more than about 0.0134) inches. At the reduced diameter portion 15 at the proximal end the core wire, the thickness of sleeve 20 increases to a maximum of about 0.002 in., but the outer diameter remains less than 0.014 in.

In distal portion 16, the sleeve 20 is also of increased thickness; but, again, at all points the thickness is controlled so that the overall diameter of the guide wire 10 will not exceed 0.014 inches. In the region of annular locking grooves 22 at the proximal end of distal portion 16, where the diameter of the core wire is about 0.010 (and grooves are about 0.0010 deep), the sleeve is about 0.0015 to 0.0020 inches thick, including the portion that fills in the grooves 22 and retains the proximal end of the sleeve 20 in position, thus maintaining an outer overall diameter of guide wire 10 not greater than about 0.014 inches.

In the distal portion 16 of guide wire 10, between the proximal end portion including grooves 22 and spring 28 at its distal end, Teflon sleeve 20 varies between about 0.0015 and 0.0030 inches in thickness. It will be recalled that the core wire 18 tapers in diameter from about 0.010, in the region including grooves 22 to about 0.0056 adjacent tip portion 12. The diameter of sleeve 20 is greater adjacent the latter so that, along the entire length of the distal portion 16, the overall diameter of guide wire 10 is more uniform than is the diameter of the core wire 18. For example, a sleeve thickness of 0.0030 adjacent tip portion 12 provides a total guide wire diameter of about 0.0115, while an 0.0015 sleeve thickness in the region adjacent proximal portion 14 provides a total guide wire diameter (about 0.013 inch) that is still less than the maximum desired diameter of about 0.014 inches.

The distal end of the sleeve 20 extends slightly beyond ring 24 and tightly engages (e.g., is heat shrunk around) the proximal approximately 1 inch portion of tip spring 28. Where spring 28 overlies and is wrapped around ring 24, its overall outer diameter is approximately 0.0105 inches. The portion of sleeve 20 surrounding spring 28 has a radial thickness of about 0.0015 inches, thus providing a maximum diameter in the tip region 12 of a little less than 0.014 inches.

In the illustrated preferred embodiment, the entire length of the Teflon sleeve 20 is heat shrunk so that the sleeve 20 tightly engages core wire 18 (or, in the tip portion, spring 28) throughout substantially the entire length of the guide wire. In the illustrated embodiment, sleeve 20 engages not only the tip and distal portions of the core wire, but proximal portion 14 also. In other embodiments, the sleeve 20 may extend only from the tip portion 12 and to (and over) the grooves 22 at the proximal end of distal portion 16. In such embodiments, one end of the sleeve 20 will tightly engage the annular locking grooves 22, the other end of the sleeve will tightly engage the proximal portion of spring 28, and the rest of the sleeve will be tightly heat-shrunk around the portions of the core wire therebetween.

Figure 4:
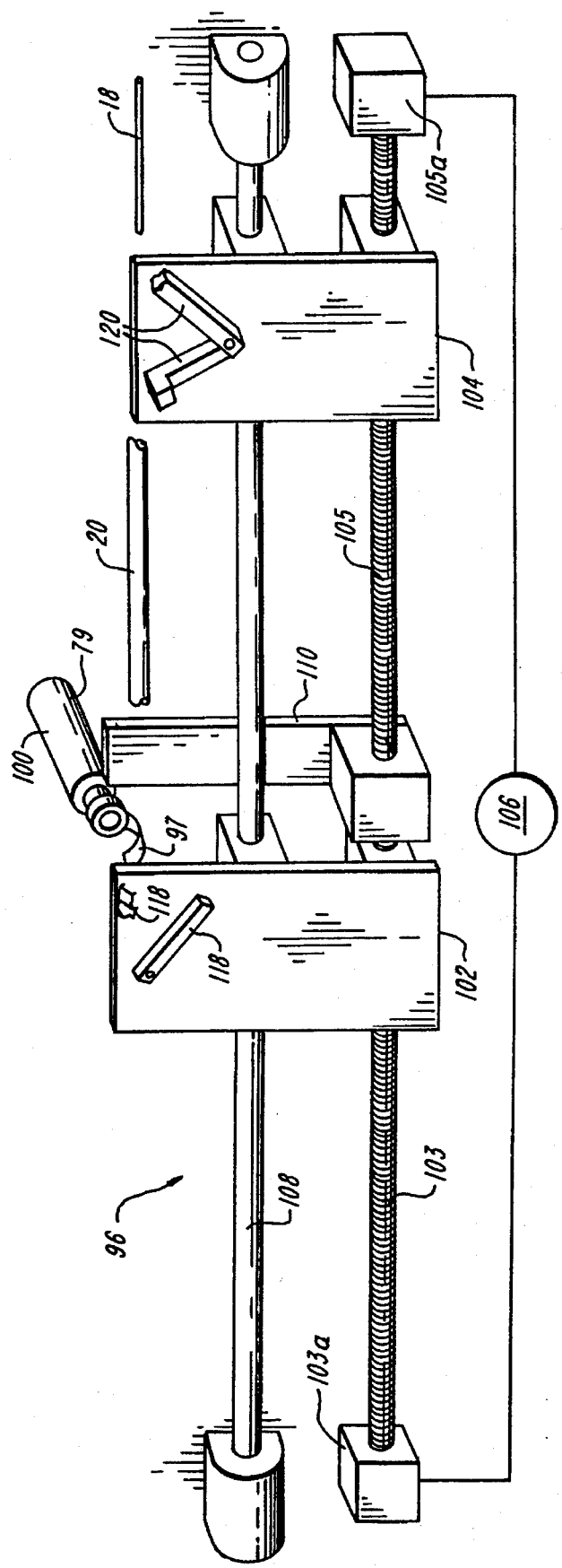
FIG. 4 shows a system useful for manufacturing the guide wire assembly of FIG. 1 and the device of FIG. 3b.

Reference is now made to FIGS. 3 and 4 which illustrate the manner in which a Teflon (or other heat shrinkable organic plastic) tube 120 is drawn over and fitted tightly around a rod or wire 118.

Figure 3A:
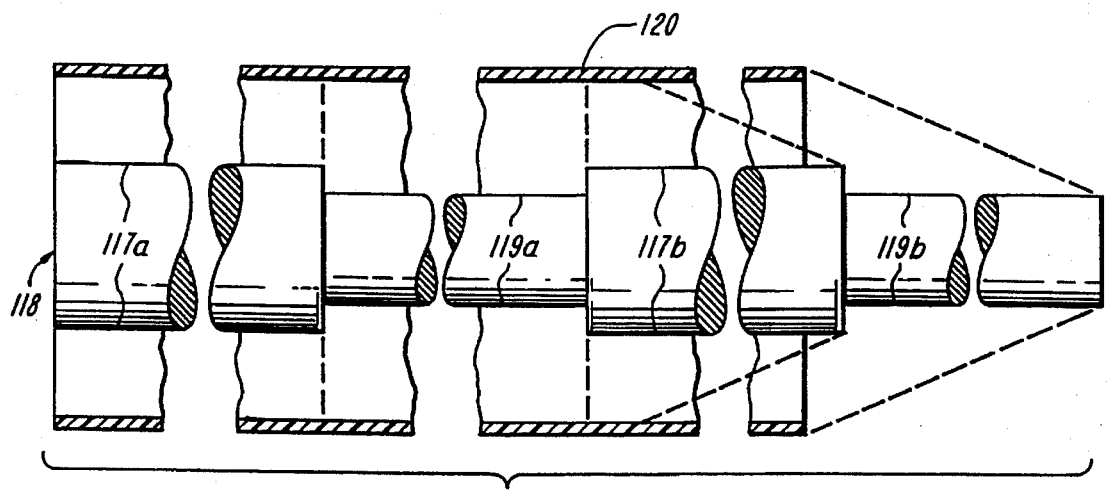
FIGS. 3a and 3b are sectional views illustrative of the practice of the present invention.

As shown in FIG. 3a, the heat shrinkable tube 120 initially has an inside diameter that is considerably larger than the outside diameter of the rod 118 around which it is fitted. Small diameter, heat-shrinkable tube is commercially available from, for example, Zeus Industrial Products of Orangeburg, S.C. The tube used in the preferred embodiment, obtained from Zeus, has an initial inside diameter of about 0.025 in. It is constructed so that, its recovered size (i.e., the size of the tube after it has been heat shrunk around the smallest diameter cylinder around which it regularly will fit with no intervening gap) is an inside diameter of 0.006 inches and a wall thickness of 0.003 in.±0.001 in. It will be recognized that the volume of the shrunk tube is, of course, substantially the same as that of the original tube; and that the wall thickness of the shrunk tube thus will vary according to the tube's final inside diameter. If, for example, the tube is shrunk around an 0.010 inch diameter rod, the final inside diameter of the heat shrunk tube will be 0.010 inches (the same as the outside diameter of the shaft) but the wall thickness will be less than that which would be obtained if it were heat shrunk around an 0.006 in. diameter rod. The precise shrinkage characteristics of the tube may vary from production lot to production lot, but have been found to be substantially constant in any single lot.

Conventionally, heat shrinkable tube has been applied to medical guide wires simply by slipping the tube over the wire and then applying heat. This produces a device in which the tube tightly surrounds and engages the underlying guide wire, at least those portions having a diameter equal to or greater than the inside diameter of the recovered tube. However, and as discussed above, the overall diameter of such a composite tube-wire will depend only on the size of the tube and wire; and the wall thickness of the shrunk tube is essentially uncontrolled.

The present invention is based on the discovery that the wall thickness of the shrunk tube may be reduced, to considerably less than that of the specified "recovered" tube and in a controlled manner, by applying tension to, and thus stretching the heated zone of, the tube relative to the inner core wire as the tube is heat shrunk. By carefully controlling the amount of stretch, the wall thickness of the shrunk tube may be controllably reduced, e.g., to 10% or less of the specified wall thickness of normal "recovered" tube, and it is also possible to obtain different desirable wall thicknesses by varying the amount of stretch. By way of example, FIG. 3b illustrates, somewhat schematically, variable wall thicknesses that may be obtained by controllably shrinking tube 120 around rod 118.

Figure 3B:
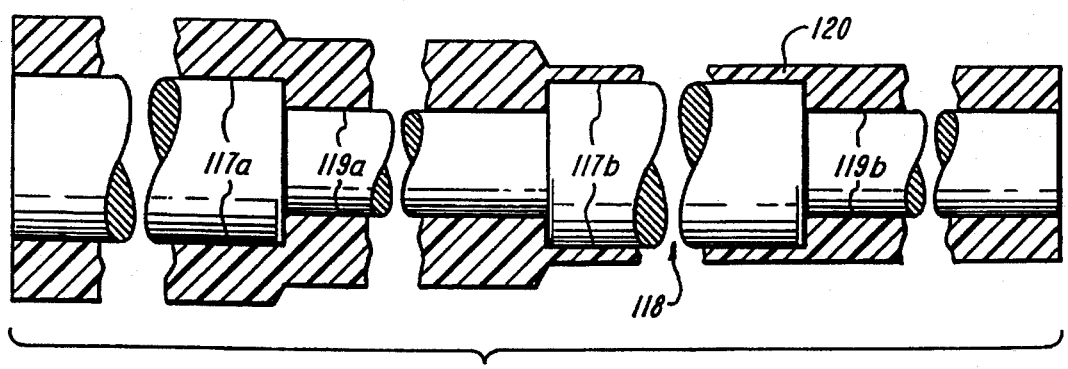

As shown in both of FIGS. 3a and 3b, rod 118 includes two portions 117a and 117b having outer diameters of about 0.010 inches, and two others, designated 119a and 119b, having reduced diameters of about 0.008 inches. Initially, and as shown in FIG. 3a, tube 120 has an inner diameter of about 0.025 inches and an 0.0006 inch thick wall. It will be noted the length of the initial length of tube 120 is considerably less than that of the rod 118 around which it is to be heat shrunk.

FIG. 3b shows the tube 120 heat shrunk around the rod 118 according to the present invention. As shown, the sizes of the rod portions 117, 119 have, of course, remained the same; and the tube tightly engages the entire outer surface of the rod. However, it will also be seen that the different portions of the heat shrunk tube 120 have substantially different wall thicknesses.

As illustrative of the present invention, the portions of the tube surrounding rod portions 117a and 119a were heat shrunk in the conventional manner, simply by applying heat. The result was that the tube surrounding portion 117a is about 0.005 in. thick; because portion 119a has a slightly smaller diameter, the tube surrounding it has a wall thickness of about 0.0055 in. It will also be seen that the overall outer diameters of the tube lengths surrounding rod portions 117a (0.022 in.) and 119a (0.019 in.) vary almost as much as do the diameters of the inner rod portions 117a, 119a themselves; the relatively slight differential in diameter is due only to the considerably smaller diameter of rod portion 119a and the natural shrink characteristics of the tube. It should also be noted, as indicated by the dashed lines in FIG. 3a, that the lengths of the unshrunk (FIG. 3a) and shrunk tube (FIG. 3b) surrounding portions 117a, 119a are substantially the same.

By way of contrast, the heat-shrunk tube surrounding and engaging portion 117b has a wall thickness of about 0.0005 inches, and the wall thickness of the shrunk tube surrounding rod portion 119b is about 0.0025 inches. Thus, the outer diameters of the tube lengths surrounding rod portions 117b and 119b are essentially the same, about 0.013 inches. With reference to the dashed lines in FIG. 3a, it will also be noted that the lengths of tube surrounding portions 117b and 119b were substantially stretched during the heat shrinking process, e.g., the heat shrunk tube around rod portion 117b in FIG. 3b was drawn form an unshrunk tube portion (FIG. 3a)

having an axial length only about ⅛ that of portion 117b, while the heat shrunk around rod portion 119b (FIG. 3b) was drawn from unshrunk tube (FIG. 3a) about half as long as the rod portion. As discussed below in connection with FIG. 4, this controlled wall thickness is provided by applying heat to successive annular zones of the tube 120 while simultaneously stretching the heated zone of the tube (each zone surrounds the portion of the rod onto which the heated tube will be shrunk) at a carefully controlled rate.

FIG. 4 illustrates, again some what schematically, a system 96 used for applying a Teflon coating of varying wall thickness to, for example, rod 118 or a core wire 18. As shown, the system includes a heater 100, a support 110 adjacent the heater, a pair of carriages 102 and 104 positioned on opposite sides of the heater 100 and support 110, and a control system 106 for controlling the speeds at which carriages 102, 104 are moved relative to the heater. The two carriages 102, 104 are mounted on a horizontal guide rod 108, and on a respective one of a pair of coaxial, threaded drives 103, 105. Each of drives 103, 105 is driven by a respective stepping motor 103a, 105a so that the speeds of rotation of the respective drive, and thus the rate at which each carriage advances, can be independently controlled.

In practice, a length of Teflon tubing 20 is slipped over the guide wire 18 around which the tube is to be heat shrunk. One end of the tubing is positioned essentially flush with the distal end of the tip portion 18 of the guide wire; and a pair of jaws 118 on carriage 102 engages the leading end, e.g., the distal approximately ⅛ inch of tip portion 12, of core wire 18 and the portion of tubing 20 surrounding it. The other, and trailing, end of the tubing is intermediate the length of the core wire and is positioned on the other side of heater 100 and support 110. A set of jaws 120 on carriage 104, which also is on the other side of heater 100 and support 110, engages the trailing end of tubing 20 but does not engage the core wire 18.

Heater 100 is a conventional hot air shrink wrap heater and includes a hot air blower 99 and a curved air flow director 97 which directs hot air from the blower 99 onto the tubing to be heat shrunk. As shown, air flow director 97 is mounted in a plane generally perpendicular to the axes of core wire 18, sleeve 20 and drives 103, 105, and is arranged so that hot air is directed onto a substantially 360 degree annular portion of tube 20 as carriage 102 draws the core wire 18 and surrounding tube 20 through the heater.

As previously indicated, the speeds at which carriage 102, 104 move relative to heater 100 vary, and are controlled by control system 106. Conventional control circuitry in control system 106 permits the speeds of rotation of the stepping motors 103, 105a, and thus the rate of axial movement of the two carriages, to be programmable and accurately controlled.

As will be seen, movement of carriage 102 (which engages the distal end of the tube 20 and wire 18) axially away from heater 100 draws the wire and surrounding tube through the plane of heater 100, thus causing hot air from the heater 100 to heat and shrink successive annular zones of the tube. It will also be seen that the speed at which wire 18 moves through the annular heat zone created by heater 100 is the same as the speed at which carriage 102 is advanced by drive 103. Typically, carriage 102 moves at a constant rate, e.g., about 6 inches/minute, thus drawing the core wire through the annular heating zone created by heater director 97 at the same speed.

Carriage 104, mounted on the other side of heater 100 and engaging the proximal end of the tube 20, moves in the same direction as carriage 102 during a heat shrinking operation. However, the speed at which controller 106 advances the carriage 104 towards heater 100 is not constant. Rather it varies from a maximum speed that is essentially the same as that of carriage 102 to a minimum speed that is substantially less than, in the preferred embodiment about ¹⁄₁₀th of that of, carriage 102.

The speed chosen for carriage 104 at any particular time during the heat shrinking operation depends on the desired wall thickness of the heat-shrunk tubing. The maximum wall thickness is obtained when carriages 102 and 104 move at the same speed. When carriage 104 moves more slowly than carriage 102, the annular zone of the tube 20 that has been heated to its plastic flow temperature in the annular heating zone of hot air deflector 97 is stretched axially, resulting in a heat shrunk tube portion having a thinner wall. The extent to which the tube thickness is reduced is directly related to the relative speeds of carriages 102 and 104. For example, if during a particular part of the tube-shrinking procedure the speed of carriage 104 is half that of carriage 102, the thickness of the shrunk tube applied during that part of the procedure will be almost exactly half that of the thickness resulting when the two carriages are moved at the same speed; similarly, the wall thickness may be reduced by about 90% by advancing carriage 104 at a speed of about ¹⁄₁₀ that of carriage 102. Tube wall thicknesses as small as 0.0001 in., or less, may been obtained.

Referring to FIGS. 3a and 3b, it will be seen that, using the system of FIG. 4, coated rod such as shown in FIG. 3b may easily be formed using the shorter, and larger initial diameter, tube shown in FIG. 3a. Initially, the rod 118 and tube 120, as shown in FIG. 3a, are mounted in the system with the leading ends of the rod and tube engaged by using 102, and the trailing end of tube 120 engaged by carriage 104. Carriage 102 is advanced all the way to the right (as viewed in FIG. 4) to adjacent the left side of support 110. Carriage 104 is positioned to the right of support 110 that the distance between it and carriage 102 is substantially equal to the length of tube 120.

To shrink tube 120 onto rod 118, heater 100 is tuned on 102 is moved the left (as viewed in FIG. 4). The carriage speed is such that heater will maintain an annular zone of the tubing 120 being drawn past the heater at the desired heat-shrink temperature. In practice, the rate of movement of carriage 102 is substantially constant throughout the entire controlled heat shrink procedure. The speed of carriage 104 is never greater than that of carriage 102 (so that there will always be at least minimal tension exerted on the tube), but this varies depending on the desired wall thickness of the shrunk tube. To form the maximum wall thickness tube (about 0.003 in.) surrounding portions 117a and 119a in FIG. 3b, the carriage 104 supporting the trailing end of tube 120 is advanced (again to the left as viewed in FIG. 4) at the same speed as carriage 102 during the period that the portions 117a and 119a are being advanced through the heating zone of heater 100. To provide the desired about 0.0005 in. thick tube around rod portion 117b, the speed of carriage 104 is reduced during the period that carriage 102 is drawing rod portion 117b through the annular heating zone, to about ¼th that of carriage 102, thereby reducing the wall thickness of the tube by about 75%. During the period that rod portion 119b is drawn through the heating zone, the speed of carriage 104 is about 60% that of carriage 102, resulting in a wall thickness (0.0015) that is about 60% that of the tube surrounding rod portion 119a.

The speed of carriage 104 is similarly varied relative to that of carriage 102 when the system 96 of FIG. 4 is used to produce the coated guide wire 10 of FIGS. 1 and 2. As previously indicated, the coaxial core wire 18 and Teflon sleeve 20 are mounted in system 98 so that the wire and coaxial tube extend from one side of heater 100 to the other, generally parallel to the axes of drives 103, 105. Jaws 118 engage both the leading ends of both the sleeve 20 and the distal end of tip portion 12 of the core wire 18, and jaws 120 engage the trailing end of the sleeve. A hook 116 on support 110 holds the wire and sleeve in position relative to heater 100.

In the initial portion of the heat shrink procedure, the tube 20 is heat shrunk around the far distal end of tip portion 12. Movement of carriages 102, 104 begins, with both carriages advancing at the same speed, as soon as the heating end of the tube reaches the required heat shrink temperature. It will be noted that this initial phase shrinks the tube around the spring 28 on the distal side of ring 24. In a later stage of the manufacturing procedure, this portion of the tubing will be removed so that the final product, as shown in FIG. 1, has no sleeve surrounding the far distal portion of the spring.

Once carriage movement has commenced, carriage 102 continues to move, away from heater 100, at a substantially constant (typically about 6 inches per minute) rate. Carriage 104 also continues to move, in the same direction (towards heater 100), but at a controlled variable rate. During the period that the sleeve 20 is being heat shrunk around the proximal portion of spring 28, carriage 102 moves at about half the speed of carriage 104, so that the wall thickness of the shrunk sleeve will be reduced to about 0.0015 inches. The portions of the core wire 18 in distal portion 16 have a diameter-(about 0.007 to 0.0056 in.) that is significantly less than the about 0.0104 inch diameter of spring 28. Accordingly, the two carriages are moved at approximately the same speed while the distal portion 12 is drawn past heater 100, so that the wall thickness of the sleeve shrunk onto the distal portion will (subject always to the limitation that the maximum overall diameter of the finished core wire 10 cannot exceed 0.014 inches) approach the recovered thickness (approximately 0.003 in.) of the sleeve, and will provide a distal portion having an overall diameter that closely approximates that of the rest of the guide wire.

The outer diameter of the grooves 22 at the distal end of the proximal portion of core wire is, as discussed previously, about 0.010 inches. Accordingly, in this region the maximum permitted sleeve wall thickness (measuring from the outer surface, and not the bottom, of grooves 22) is slightly less than 0.002 inches. To provide this thickness, carriage 104 is slowed, typically to a speed of about two-thirds that of carriage 102 while this portion of the sleeve and core wire are being advanced through the heat zone of heater 100. Similar relative speeds are employed when sleeve is being heat shrunk around the reduced diameter portion 15 at the extreme proximal end of the core wire.

Between reduced diameter portion 15 and grooves 22, the core wire 18 has an outer diameter of about 0.0128 in. and only a very thin coating can be permitted if the final diameter is to be held below the maximum 0.014 inches. Thus, carriage 104 is slowed to a speed of only about 1/10 that of carriage 102 when the sleeve is being heat shrunk around this portion of the core wire, and the wall thickness of the shrunk sleeve is only about 0.0003 inches, about 10% of the sleeve's normal recovered wall thickness.

AS previously indicated, the precise relative carriage speeds required to produce a shrunk sleeve of the desired wall thickness will depend, among other things, on the particular material from which the sleeve is made. It will thus be recognized that the relative speeds mentioned above are necessarily illustrative, and that the exact speed desired for any application must, to some extent, be determined through trial and error.

It will also be recognized that variations may be made in the system 96 used to controllably heat shrink the sleeve 20 onto the core wire. For example, it is important that (a) the rate of relative movement between heater 100 and the jaws 118 engaging the distal end of the core wire 18 and sleeve 20, and (b) the rate of relative movement between heater 100 and the jaws 120 engaging the trailing end of sleeve 20, be controlled independently of each other. It is also important that at least one of the two rates be controllably variable. However, it is not necessary that both jaws move or that speed of the jaws 120 engaging the trailing end of the sleeve be varied. In other systems embodying the invention, for example, the jaws 120 may be fixed, both the heater and jaws 118 may move away from jaws 120, and only the speed of jaws 118 may be varied.

These and other variations will be within the scope of the following claims.

What is claimed is:

1. A guide wire including a core wire surrounded by a polymeric plastic sleeve and having a proximal portion, a distal portion, and a tip portion on the side of said distal portion most distant from said proximal portion, said core wire comprising a proximal portion of substantially constant diameter within the proximal portion of said guide wire, and a distal portion of varying diameters less than the diameter of said proximal portion thereof within the distal portion of said guide wire, a helical spring extending from adjacent the distal end of said tip portion of said guide wire to a point within, and adjacent the distal end of, said distal portion of said guide wire, said sleeve surrounding and being attached by heat shrinking to (a) the portion of the exterior surface of said spring within said distal portion of said guide wire and, (b) the exterior annular surface of said core wire in an area axially spaced therefrom and adjacent the proximal end of said distal portion of said guide wire, (c) the distal portion of said core wire therebetween, and variations in the overall diameter of said sleeve in said distal portion of said guide wire being less than said variations in the diameter of the portion of said guide wire surrounded by said sleeve.

2. The guide wire of claim 1 wherein said sleeve surrounds and is attached by heat shrinking to at least a major length of said proximal portion of said core wire, said sleeve having substantially less thickness in said proximal portion of said guide wire than in the distal portion of said guide wire.

3. The guide wire of claim 2 wherein the thickness of said sleeve in said proximal portion of said guide wire is not more than about 0.001 in.

4. The guide wire of claim 1 wherein said core wire includes annular grooves adjacent the proximal end of the distal portion thereof, and said sleeve protrudes inwardly into said grooves.

5. The guide wire of claim 1 wherein said core wire includes an annular ring adjacent the distal end of said distal portion of said core wire, and said spring is attached to the periphery of said annular ring.

6. The guide wire of claim 5 wherein said tip portion of said guide wire includes a rounded tip attached to the distal end of said core wire and the distal end of said helical spring.

7. A method of producing a guide wire including a core wire surrounded by a heat shrunk polymeric plastic sleeve of variable wall thickness, said method comprising the steps of:

inserting said core wire into a said sleeve having an inner diameter greater than the outer diameter of said core wire;

applying heat to said sleeve to heat shrink said sleeve around said core wire, said heat being applied to successive axially spaced annular zones of said sleeve;

causing relative movement of (i) said core wire and a distal portion of said sleeve relative and (ii) said zones in a first direction generally parallel to the axis of said wire and at a first rate of speed while said heat is being applied;

causing relative movement of a proximal portion of said sleeve and to said zones in said direction and at a second rate of speed that is not grater than said first rate while said heat is being applied; and varying at least one of said first rate and said second rate while said heat is being applied thereby to vary the thickness at which said sleeve is heat shrunk onto said core wire.

8. The method of claim 7 wherein said sleeve is a polytetrafluroethylene.

9. The method of claim 7 including the steps of providing a heater for applying said heat, and disposing a pair of jaws on opposite sides of said heater, one of said jaws being arranged to engage said distal portions of said core wire and said sleeve and the other of said jaws being arranged to engage said proximal portion of said sleeve, and each of said jaws being movable relative to said heater.

10. The method of claim 7 wherein said rate is varied such that the thickness of said heat shrunk sleeve varies between a maximum thickness and a minimum thickness that is not more than about one-half said maximum thickness.

11. The method of claim 7 wherein said minimum thickness is not more than about 10% of said maximum thickness.

12. The method of claim 7 wherein said core wire varies in diameter along the length thereof surrounded by said sleeve, and including the step of varying said at least one rate such that the overall diameter of the portion of said core wire surrounded by said heat shrunk sleeve is substantially constant.

13. The method of claim 7 wherein said sleeve and said distal portion of said core wire are moved away from said zones at said first rate of speed, and said proximal portion of said sleeve is moved towards said zones in said first direction at said second rate of speed.

14. A method of producing a composite product including a longitudinally extending member surrounded by a heat shrunk polymeric plastic sleeve of variable wall thickness, said method comprising the steps of:

inserting said member into a said sleeve having an inner diameter greater than the maximum transverse cross-sectional dimension of said member;

applying heat to said sleeve to heat shrink said sleeve around said member, said heat being applied to successive axially spaced annular zones of said sleeve;

causing relative movement of (i) a distal portion of said sleeve relative to (ii) said zones in a direction generally parallel to the axis of said member and at a first rate of speed while said heat is being applied;

causing relative movement of a proximal portion of said sleeve and to said zones in a direction generally parallel to said direction and at a second rate of speed that is not greater than said first rate while said heat is being applied; and, varying at least one of said first rate and said second rate while said heat is being applied thereby to vary the thickness at which said sleeve is heat shrunk onto said member.

15. The guide wire of claim 1 wherein the wire forming said spring is rectangular in cross section.

* * * * *